(12) United States Patent
Kiderman et al.

(10) Patent No.: US 7,448,751 B2
(45) Date of Patent: Nov. 11, 2008

(54) PORTABLE VIDEO OCULOGRAPHY SYSTEM WITH INTEGRAL LIGHT STIMULUS SYSTEM

(75) Inventors: Alexander D Kiderman, Pittsburgh, PA (US); John Howison Schroeder, Pittsburgh, PA (US); Thomas C. Joos, Pittsburgh, PA (US); Floris L. Wuyts, Boom (BE); Steven T Moore, New York, NY (US); Hamish G MacDougall, New South Wales (AU)

(73) Assignee: Neuro Kinetics, Inc., Pittsburgh, PA (US)

( * ) Notice: Subject to any disclaimer, the term of this patent is extended or adjusted under 35 U.S.C. 154(b) by 0 days.

(21) Appl. No.: 11/549,185

(22) Filed: Oct. 13, 2006

(65) Prior Publication Data
US 2007/0121068 A1    May 31, 2007

Related U.S. Application Data

(62) Division of application No. 10/704,529, filed on Nov. 7, 2003.

(51) Int. Cl.
*A61B 3/10* (2006.01)
*A61B 3/14* (2006.01)
*A61B 3/02* (2006.01)

(52) U.S. Cl. .................. 351/205; 351/206; 351/216; 351/221; 351/243

(58) Field of Classification Search .................. 351/205, 351/206, 211, 216, 221, 222, 237, 243, 245
See application file for complete search history.

(56) References Cited

U.S. PATENT DOCUMENTS

| | | | |
|---|---|---|---|
| 5,070,883 A | 12/1991 | Kasahara | |
| 5,252,999 A * | 10/1993 | Sukigara et al. | 351/221 |
| 5,365,941 A | 11/1994 | Yoshimatsu | |
| 5,481,622 A | 1/1996 | Gerhardt | |
| 5,491,492 A | 2/1996 | Knapp | |
| 5,704,369 A | 1/1998 | Scinto | |
| 5,838,420 A | 11/1998 | MacGregor Donaldson | |

(Continued)

OTHER PUBLICATIONS

Maria Fontanazza, Device Eases Diagnosis of Concussions and Other Cognitive Conditions, http://www.devicelink.com/mddi/archive/05/07/010.html.

(Continued)

*Primary Examiner*—Scott J. Sugarman
*Assistant Examiner*—Brandi N Thomas
(74) *Attorney, Agent, or Firm*—Blynn L. Shideler; Krisanne Shiedeler; BLK Law Group

(57) ABSTRACT

A goggle based light-weight VOG system includes at least one digital camera connected to and powered by a laptop computer through a firewire connection together with an integral visual light stimulus source. The digital camera may digitally center the pupil in both the X and Y directions. A calibration mechanism may be incorporated onto the goggle base. An EOG system may also be incorporated directly into the goggle. The VOG system may track and record 3-D movement of the eye, track pupil dilation, head position and goggle slippage. An animated eye display provides data in a more meaningful fashion. The VOG system is a modular design whereby the same goggle frame or base is used to build a variety of digital camera VOG systems.

11 Claims, 5 Drawing Sheets

U.S. PATENT DOCUMENTS

| | | | |
|---|---|---|---|
| 5,892,566 A | 4/1999 | Bullwinkel | |
| 5,942,954 A | 8/1999 | Galiana | |
| 5,963,300 A | 10/1999 | Horwitz | |
| 5,983,128 A | 11/1999 | Baudonniere | |
| 6,003,991 A * | 12/1999 | Viirre | 351/206 |
| 6,024,707 A | 2/2000 | Scinto | |
| 6,033,073 A | 3/2000 | Potapova | |
| 6,077,237 A | 6/2000 | Campbell | |
| 6,090,051 A | 7/2000 | Marshall | |
| 6,099,124 A | 8/2000 | Hidaji | |
| 6,113,237 A | 9/2000 | Ober | |
| 6,120,461 A | 9/2000 | Smyth | |
| 6,162,186 A | 12/2000 | Scinto | |
| 6,213,943 B1 | 4/2001 | Abreu | |
| 6,231,187 B1 | 5/2001 | Munoz | |
| 6,367,932 B1 | 4/2002 | Donaldson | |
| 6,402,320 B1 | 6/2002 | Borchert | |
| 6,459,446 B1 | 10/2002 | Harman | |
| 6,467,905 B1 | 10/2002 | Stahl | |
| 6,524,581 B1 | 2/2003 | Adamis | |
| 6,551,575 B1 | 4/2003 | Greenspan | |
| 6,574,352 B1 | 6/2003 | Skolmoski | |
| 6,609,523 B1 | 8/2003 | Anthony | |
| 6,629,935 B1 | 10/2003 | Miller | |
| 6,637,883 B1 | 10/2003 | Tengshe | |
| 6,652,458 B2 | 11/2003 | Blazey | |
| 6,659,611 B2 | 12/2003 | Amir et al. | |
| 6,669,341 B2 | 12/2003 | Wirth | |
| 6,697,894 B1 * | 2/2004 | Mitchell et al. | 710/73 |
| 6,748,275 B2 | 6/2004 | Lattner | |
| 6,796,947 B2 | 9/2004 | Watt | |
| 6,800,062 B2 | 10/2004 | Epley | |
| RE38,668 E | 12/2004 | Edwards | |
| 2002/0027779 A1 * | 3/2002 | Cassarly et al. | 362/231 |
| 2002/0085174 A1 | 7/2002 | Bolger et al. | |
| 2002/0171805 A1 * | 11/2002 | Odom et al. | 351/221 |
| 2002/0175880 A1 * | 11/2002 | Melville et al. | 345/8 |
| 2003/0028081 A1 | 2/2003 | Blazey et al. | |
| 2004/0181168 A1 | 9/2004 | Plant et al. | |
| 2005/0024586 A1 | 2/2005 | Teiwes et al. | |
| 2005/0079636 A1 | 4/2005 | White et al. | |
| 2005/0101877 A1 | 5/2005 | Miller et al. | |
| 2005/0110950 A1 | 5/2005 | Thorpe et al. | |
| 2005/0216243 A1 | 9/2005 | Graham et al. | |
| 2006/0098087 A1 | 5/2006 | Brandt et al. | |

OTHER PUBLICATIONS

Jason S. Babcock, Jeff B. Pelz, Building a lightweight eyetracker, http://www.cis.rit.edu/people/faculty/pelz/publications/ETRA04_babcock_pelz.pdf, 2004.

D. Zhu et al., Computer Methods and Programs in Biomedicine 59 (1999), pp. 146-157.

Hamish G. MacDougall, Applicants description of Prior Art Systems, Applicants internal memo regarding Prior Art.

Moore et al., A geometric Basis for Measurement of Three-Dimensional Eye Position Using Image Processing, pp. 445-459, Vision Res. vol. 36.

* cited by examiner

PORTABLE VIDEO OCULOGRAPHY SYSTEM WITH INTEGRAL LIGHT STIMULUS SYSTEM

RELATED APPLICATIONS

This application is a divisional application of pending U.S. patent application Ser. 10/704,529 filed Nov. 7, 2003 entitled Portable Video Oculography System and which published May 12, 2005 as publication number 2005-0099601, which publication is incorporated herein by reference.

BACKGROUND OF THE INVENTION

1. Field of the Invention

The present invention relates to clinical eye tracking systems, and more particularly to a self-contained, portable video-oculography goggle system with integral light stimulus system.

2. Background Information

Accurate eye position recording and monitoring in three dimensions (3D-yaw, pitch and torsion rotation about line of sight) is a significant clinical diagnostic tool in the field of vestibular disorders such as vertigo and other neurological disorders. A non-invasive technique for recording eye position relative to the head is to use a camera to record eye position relative to the head, known as videoculography or VOG. VOG systems are used by Vestibular Researchers, Ophthalmologist, Otolaryngologists, Physical Therapists, Neurologists, Audiologists, Balance Clinicians, Neurophysiologists, Physiologists, Neuroscientists, Occupational Therapists, and others. Image processing software is utilized to interpret the images to provide objective data of eye position. This is described in "A GEOMETRIC BASIS FOR MEASUREMENT OF THREE-DIMENSIONAL EYE POSITION USING IMAGE PROCESSING" Vision Res. Volume 36. No. 3, Moore et al., pp 445-459, 1996, which is incorporated herein by reference.

The existing VOG systems can be categorized as either earth mounted or head mounted systems. The oldest method uses earth fixed cameras and attempt to limit movement of the head. The relative movement of the head and the camera would be interpreted as eye movement. These systems attempt to stabilize or immobilize the head with head holders, head rests, chin rests, or bite bars. Although archaic, this type of system is still used extensively in some laboratories and many clinical environments. The biggest disadvantage of these systems is the inability to remove all head movement. Even the smallest head movements (e.g. resulting from breathing, talking, involuntary postural modification, and from fatigue etc.) cause significant inaccuracy in the measured eye movement. These systems are particularly unsuitable when inertial stimuli (e.g. a rotational chair) are delivered to a subject in order to produce vestibular responses, since these stimuli also tend to generate head movement. This equipment is often heavy and bulky since it must be strong enough to support and attempt to restrain the head of a subject.

Another classification of earth mounted VOG systems are systems that attempt to measure eye movement using a space fixed (earth mounted) camera without a head holder mechanism. In general, these systems attempt to deal with head movement by first tracking the head and then the eye within the head. In practice, a subject must actively suppress their head movements to within a small range of translations in order to stay within view of the camera. Further, rotations of the head are quite difficult to detect using image processing and so these systems suffer from an inability to distinguish between a change of eye position in the head or a change of head position during maintained gaze. These systems must also use a wide-angle lens in order to digitize an image that includes the head movements. Consequently, little picture resolution is available for the analysis of the eye position. As a result of these limitations, these systems are generally only able to measure horizontal and vertical changes in relative eye/head position Another earth mounted VOG system attempts to measure the eye position by first tracking the position of the head and then moving a camera or mirrors to get an image of the eye with higher magnification and resolution. These systems also share many of the disadvantages of the other VOG earth fixed camera systems including the inability to accurately distinguish between head translation and rotation. Further, the mechanisms used can be complicated expensive noisy and distracting.

A second classification of VOG systems is the head mounted system. In one type of head mounted VOG system, head mounted cameras are supported by an adjustable headband often modified from the insert from a mining or welding helmet. The cameras may be mounted above the eyes and are directed down towards hot mirrors that reflect an infrared image of the eye. Head mounted eye movement recording systems are less prone to the errors from head movement, because the cameras move with head. Further this method for attaching the cameras to the head is particularly popular because the headsets can be easily fitted to any subject without modification. The camera mounting position above the eyes also seems fairly natural because hardware tends to stick up into the air. This placement keeps the centre of gravity closer to the head and reduces the inertial lag on yaw head movements. Despite these advantages, all head mounted video eye movement measurement systems obviously suffer from the need to wear equipment and be connected, via leads, to the analysis hardware. Further, the headband can be painful if it is tightened enough to effectively suppress slippage of the headset during head movement.

The camera may also be mounted to the side of the headband head mounted VOG systems. The main advantage of mounting cameras to the side rather than above the eyes is that the centre of mass of the headset tend to be further back towards the head and so these headsets don't tends to pitch the subject's head forward as much as some other arrangements. This camera position also can provide better power supply and data output access (i.e. the electrical and control feeds). The main disadvantage of this mounting position is that the headsets tend to become quite wide. These headsets tend to move relative to the head during the yaw head movements that are common during vestibular testing.

The camera may also be mounted in front of headband in the headband head mounted VOG systems. The main advantage from mounting cameras towards the front of the subject is that no hot mirrors are required to reflect an image of the eye into the cameras. This lack of hot mirrors simplifies the construction and adjustment of the headsets and may improve the quality of video images. However, while front mounted cameras might suit light occluded systems where darkness prevents the subject from seeing them, they don't suit most video headsets that use headbands because these may not have an open field of view. Apart from the obstruction to vision, cameras in front of the subject can provide visual suppression and orientation cues that may affect their eye movement responses. The headsets with front mounted cameras also tend to have a centre of gravity that is further away from the head.

In place of the headband, some head mounted VOG systems utilize goggles, similar to those on diving masks, in order to attach cameras to the subjects face. These headsets benefit from a silicon skirt that conforms to the face and stabilizes the cameras. Goggles also leave the head clear for the use of other devices that may be utilized in various clinical applications. Another advantage of goggles is that they are well suited for the construction of light occluding headsets as well as those with an open field of view, or those that are convertible between the two. The disadvantage of goggles style head mounted VOG systems is that they can be uncomfortable if the cameras and other hardware is to heavy and ways down on the subjects face.

Some research head mounted VOG systems use video cameras mounted on the headset with individually molded plastic or fiberglass masks. These masks are particularly stable and good at suppressing relative camera and head movement. Molded masks also tend to spread the weight of the video headset over a large surface area and do not produce the pressure points characteristic of some other methods. However, individually molded masks can be time-consuming and costly to make and are therefore not convenient for the clinical testing of large numbers of patients. Hybrid masks that combine a headband and standard molded mask section do not have these disadvantages but do not seem to benefit from the advantages either.

Another head mounted VOG system utilizes a helmet for camera mounting. The helmet style video headset benefits from a more even distribution of weight over the top of the head and from the balance provided by more weight towards the back. Helmet style video headsets are heavier than many other systems and so they tend to shift around during vigorous head movement. They are also quite bulky and prevent the application of head holders.

Another head mounted VOG system utilizes standard glasses construction (i.e. spectacle) for camera mounting. The advantages of spectacle type video headsets are that they can be very small and light, and are easily transportable. The disadvantages of this method include the discomfort from heavy equipment resting on the bridge of the nose. With very small contact area, spectacles can also be prone to movement relative to the head in response to inertial forces.

There remains a need for truly portable VOG systems. Further, there continues to be a need for accurate meaningful output for the clinicians in VOG systems without significant discomfort to the patients.

The above discussion concentrates on the deficiencies in the mechanical design of existing VOG systems. In addition to those issues, existing VOG systems are designed as one-of-a kind testing structures. This approach leads to expensive end products. Existing VOG systems also suffer from poor camera design, camera power supply issues, data transfer problems.

Analog cameras in existing VOG systems provide data regarding eye position for analysis as is known in the art. During testing the visual image of the eye(s) is often displayed in real time as a method for the clinician to follow and interpret the data. In other words a real video image of the patient is displayed with a graphed display of the data (e.g. a chart of eye vertical and horizontal position change over time). These may also be recorded for later review. The realistic eye image of the video does not always easily illustrate movement.

Clinicians have stated that existing VOG systems on the market suffer from the following drawbacks: the excessive weight of goggles, they can't be used with droopy eyelids; difficulty with set-up; torsional measurements not available; lack of the sensor for head positioning; difficulty in viewing eyes; limited in the number of targets presentable to the patient; low sampling rates; software limitations and inflexibility; no ability to focus the camera; and concerns over resolution.

There is a need to address at least some of these problems as well and still provide a portable, affordable VOG system providing accurate meaningful output for the clinicians in VOG systems.

SUMMARY OF THE INVENTION

The above stated objects achieved with a portable VOG system according to the present invention. A video oculography system according to one aspect of the invention includes a light-weight head mounted base, such as goggles, adapted to be attached to a patient's head, at least one camera attached to the base, a controller coupled to the at least one camera, the controller providing power and control signals to each camera and receiving and storing data signals there from, at least one camera light source attached to the base, wherein each camera light source is associated with one camera attached to the base and is configured to illuminate the patient's eye sufficient for the camera to obtain an image of the patient's eye, and at least one visual stimulus light source attached to the base and distinct from the at least one camera light source, wherein each visual light source is configured to selectively supply a visual stimulus to a patients eye that is distinct from the camera light source.

In one non-limiting embodiment of the invention goggles forming the base may provide an occluded environment for the patient's eyes. Further, at least two visual stimulus light sources may be provided for each patient's eye in one aspect of the invention. The camera light sources and the visual stimulus light sources may be formed in an annular array for at least one of the patient's eyes. The system may further include a laser attached to the base, wherein the laser is visible to the clinician while the patient is wearing the head mounted base. The system may provide that the camera light sources have a light wavelength that is distinct from the light wavelength of the visual stimulus light sources, such as where the camera light sources are infrared light sources. In one non-limiting embodiment the camera light sources are formed from a plurality of infrared LEDs and the visual stimulus light sources are formed from a plurality of visible light LEDs. In a further non-limiting embodiment the visual stimulus light source includes a fiber optic light that may be centered on the camera.

According to one aspect of the invention the video oculography system according to the invention includes a light-weight head mounted base adapted to be attached to a patient's head forming an occluded environment for at least one of the patient's eyes, at least one camera attached to the base directed at the patient's eye in an occluded environment, a controller coupled to the at least one camera, the controller providing power and control signals to each camera and receiving and storing data signals there from; and an array of light sources directed at the patients eye in the occluded environment.

According to one aspect of the invention the video oculography system according to the invention includes a modular video oculography system that comprises a light-weight head mounted base adapted to be attached to a patient's head, a plurality of cameras, each selectively attached to the base, wherein the plurality of cameras may be selectively attached to the base to form one of an occluded monocular system and an occluded binocular system, a controller providing power and control signals to each camera attached to the base and receiving and storing data signals there from, and an annular array of light elements associated with each camera.

The portable VOG system according to the present invention is a goggle head mounted system with at least one digital camera of at least 30 hz generally connected to and powered by a computer through a firewire connection. The computer may be a laptop portable computer (generally less than about 3 kilograms), whereby the entire system will be less than 8 kilograms and preferably less than 5 kilograms, and most preferably less than 4 kilograms. The weight of the goggles is critical in that the lightweight goggles have lower inertia and move less improving accuracy of the system. The low inertia goggles of the present invention provide a 3d system and weigh less than 500 grams, preferably less than 300 grams and most preferably less than 200 grams.

The digital camera will allow for digital centering of the patient's pupil at least in one direction through concentrating on the region of interest, and preferably in two directions (X and Y). The use of digital centering eliminates the need for a mechanical adjustment mechanism (e.g. a slide) in the given direction. Using digital centering for both the X and Y (yaw and pitch) directions eliminates any gross adjustment in those directions.

The VOG system according to the present invention incorporates a head fixed calibration mechanism in the form of an integrated laser pointer on the goggle base or camera housing. The calibration mechanism is incorporated directly into the goggle base and powered from the same source powering the digital cameras. This construction greatly simplifies and quickens the calibration steps and improves accuracy thereof.

The VOG system according to the present invention further incorporates an EOG (Electro-OculoGraphy) system that can operate independent of or preferably in conjunction with the VOG system to supplement the acquired data. The EOG system is incorporated directly into the goggle base and powered from the same source powering the digital cameras.

The VOG system of the present invention is designed to track and record 3-D movement of the eye (generally movement in an X-Y plane and eye rotation or torsion about the line of sight) generally as found in some of the prior art systems, however the present digital based system is designed to further track pupil dilation, providing the clinician with further critical data for diagnostic testing. The pupil size can be calculated as a byproduct of pupil center calculation using existing pupil center locating technology.

The VOG system of the present invention may further include a head tracking sensor to track and record a patient's head position. The head position data may be used to supplement other data and possibly to assist in calculating any goggle slip that occurs. Essentially by knowing the goggle mass and inertia values relative to the patient and the head movement data through a head position sensor an algorithm may be developed to approximate the goggle position/slippage (e.g. approximating the static and kinetic friction between the skirt of the goggle and the patient and the force applied by the goggle strap an appropriate algorithm may be developed). Calculated goggle slip can then be removed from the eye movement data through appropriate software.

The VOG system of the present invention is designed to provide an animated eye display with variable, clinician controlled gain to the clinician to provide data in a more meaningful fashion. Specifically, subtle movements are more easily visualized. The animated eye can more easily convey position and can include a scaling factor, or gain, to supplement the illustrated animated eyes. The animation may include visible indicia, e.g. cross hairs at the pupil center in front view. In plan view an animated eye may include a line of sight to visibly illustrate where a given eye is focused on.

The VOG system of the present invention is intended to be a modular design in that the same goggle frame or base is used to build monocular front mounted digital camera VOG systems, binocular front mounted digital camera VOG systems, monocular side or top mounted digital camera VOG systems, binocular side or top mounted digital camera VOG systems, etc.

These and other advantages of the present invention will be clarified in the description of the preferred embodiment together with the attached figures were like reference numeral represent like elements throughout.

DESCRIPTION OF THE PREFERRED EMBODIMENTS

Figure 1:
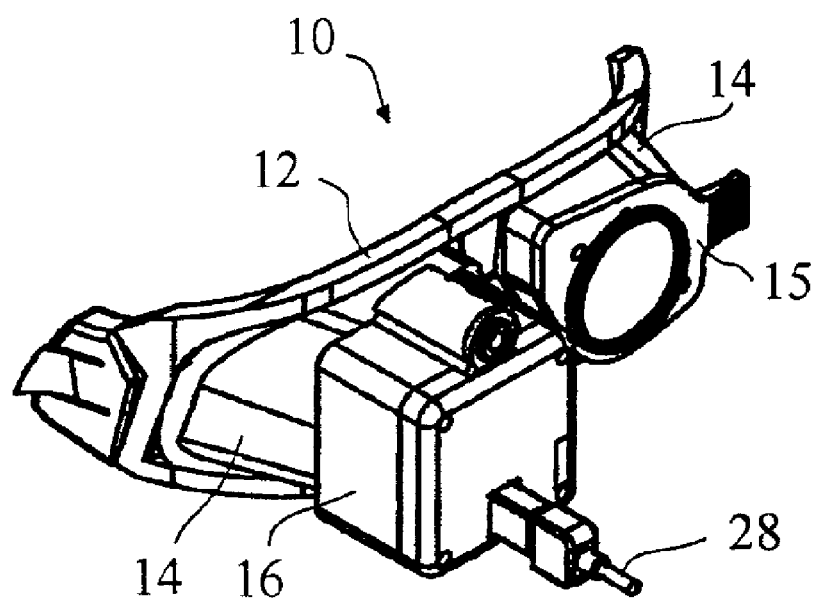
FIGS. 1-3 are perspective views of a goggle for the goggle based VOG according to the present invention.
Figure 2:
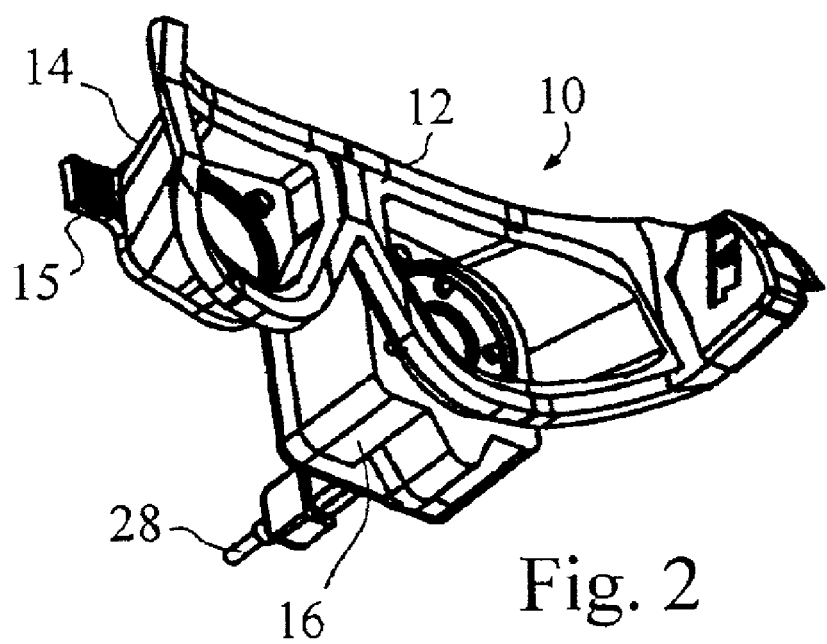
Figure 3:
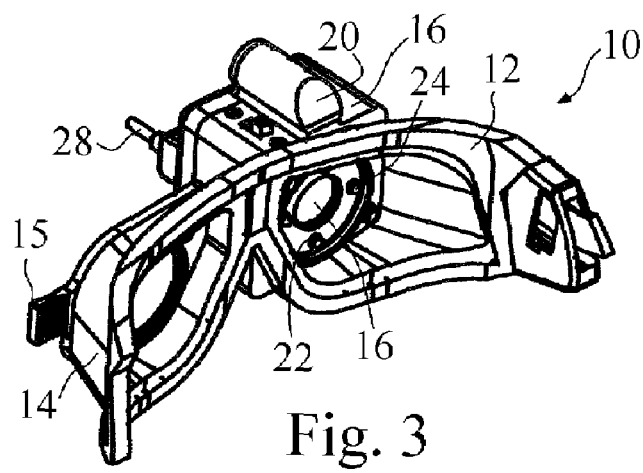

FIGS. 1-4 illustrate a goggle headset for a VOG system 10 according to the present invention. The system 10 is a goggle based system using a goggle frame or base 12 for fitting onto the patient. The base 12 is essentially a frame for swimming or diving goggles such as manufactured by Technisub S.p.A., and described in U.S. Pat. No. 5,915,541 which is incorporated herein by reference. The base 12 provides a skirt for distributing the forces around the face and which conforms to the face, and which can be critical for occluded VOG systems. The occluded systems simply refer to systems where external light is blocked out for at least one eye. The base 12 is far more universal than an individual face formed mask.

Each eye portion of the base 12 includes a mounting member 14. The mounting members 14 are used for constructing any of a variety of front mounted VOG systems in accordance with the present invention. One member 14 may be left open to provide a field of view of at least 30 degrees horizontal and 30 degrees vertical. Alternatively one member 14 may be covered with a cap 15 to provide an occluded monocular system. Another embodiment could provide one or two caps 15 each with an optical frenzel lens, wherein the clinician can view the patient's eye through frenzel lens. In the VOG system shown in FIGS. 1-4 one member 14 receives a digital camera unit 16. Both members 14 could receive a digital camera unit 16 forming an occluded binocular front mounted VOG system according to the present invention.

The digital camera unit 16 includes a digital camera operating at least at 30 hz (30 frames per second), although 120 hz-200 hz cameras and even higher are available. Another aspect of the present invention is the concept of utilizing the same camera 16 and increasing the operating cycles by trading off the total resolution. As a representative example, if the pupil location were simulated with ten, five or even points (i.e. a very low resolution image of the eye) than the speed with the same camera can be drastically increased. Such limited resolution would be impractical for most diagnostic applications, but may be suitable for a sports training application (e.g. baseball batters or golf players). Suitable cameras for the unit 16 are sold under the name iBot camera, Stealth-Fire camera, Firefly II, and Scorpion camera, as a representative sample. Some of these cameras are sold through Point Grey and can be found at http:/www.ptgrey.com/. These cameras typically operate on a regulated 3.3V DC and have a resolution of at least 640×480 although higher resolutions cameras such as 1024×640 are also currently available. A 480×320 resolution image (or less) is available and may be sufficient particularly where one desires a higher transmission rate.

Figure 4:
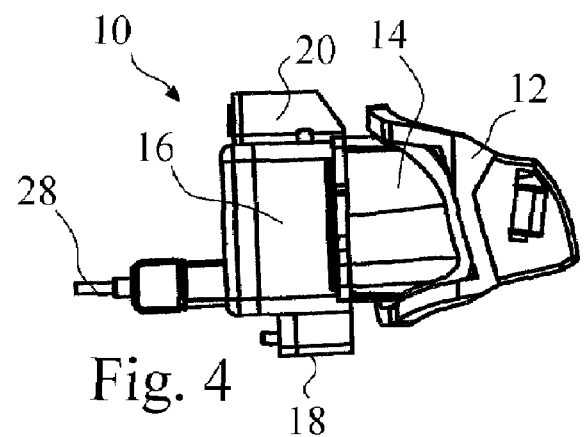
FIG. 4 is a schematic sectional side view of the goggle illustrated in FIGS. 1-3.
Figure 6:
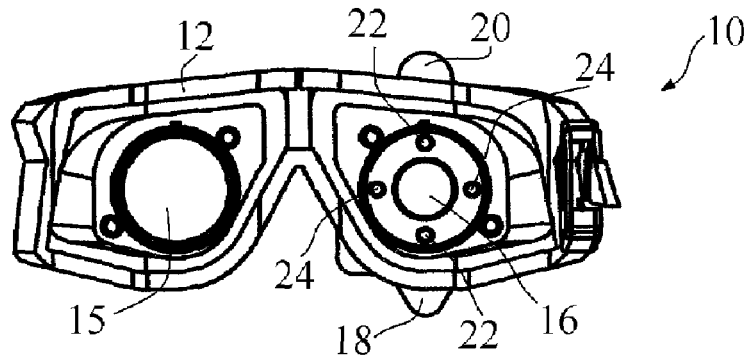
FIG. 6 is a front view of an eye tracking camera assembly for use in the VOG system according to the present invention.
Figure 5A:
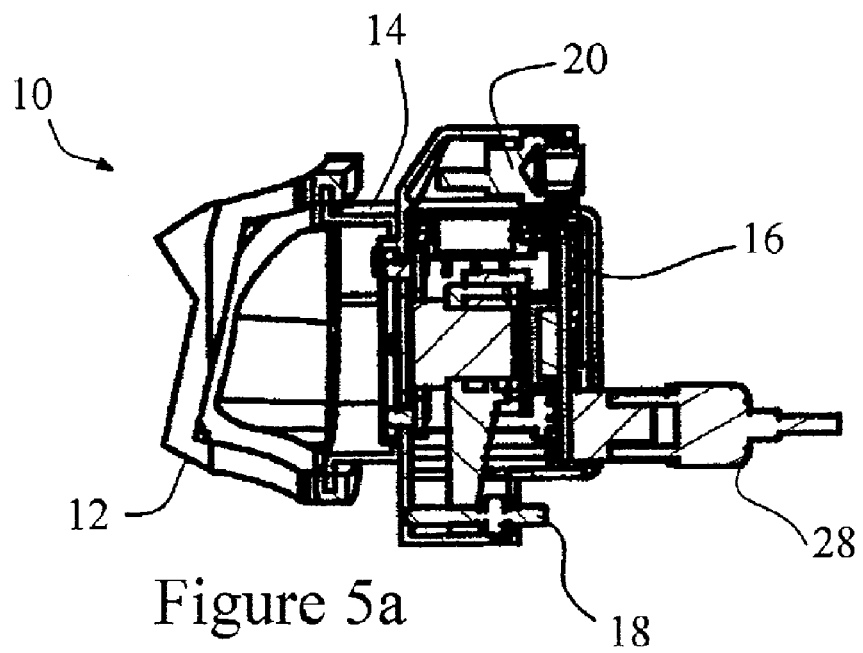
FIGS. 5a and b are schematic sectional side views of alternate adjustment mechanisms for a camera used in the goggle of FIGS. 1-3.
Figure 5B:
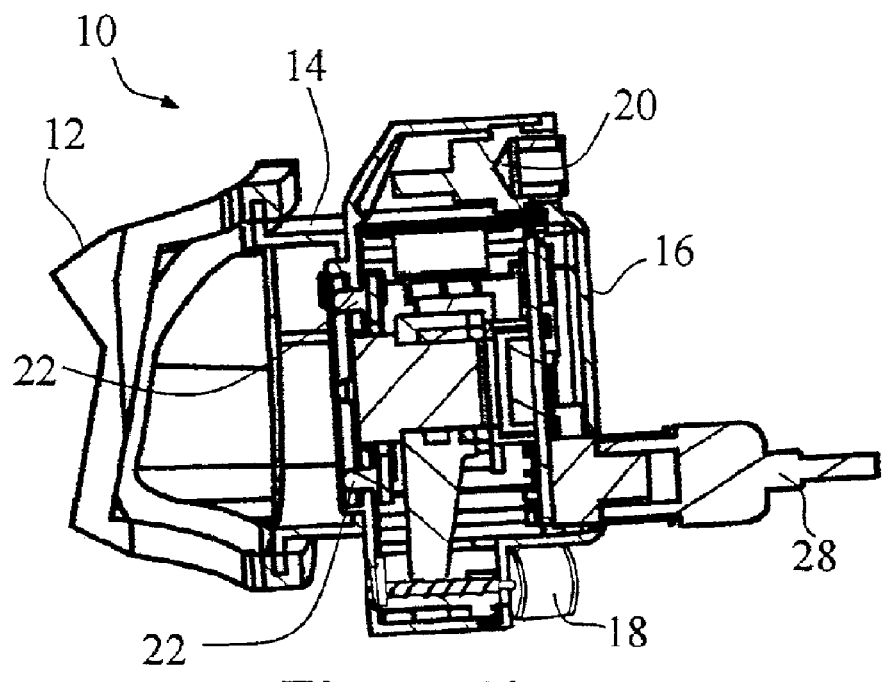

As shown in greater detail in FIGS. 4 and 5*a* and *b*, the camera units 16 include an outside mounted Z axis adjustment mechanism 18. The adjustment mechanism 18 allows for the focus to be adjusted for the camera unit 16 while the goggle base 12 is on the patient (e.g. from outside of the goggle base 12) without allowing light to enter. The adjustment mechanism 18 is effectively a slide mounting for the camera lens with an adjusting screw for the displacement of the slide in FIG. 5*a*. Alternatively the mechanism 18 may be a stepper motor, such as in a computer hard drive, as shown in FIG. 5*b*.

Regarding the centering of the camera in the camera unit 16 onto the pupil, the use of high resolution digital cameras allows this to be accomplished digitally. Specifically when the pupil location is identified, such as by using the algorithm described in the "A GEOMETRIC BASIS FOR MEASUREMENT OF THREE-DIMENSIONAL EYE POSITION USING IMAGE PROCESSING" article discussed above, the software will crop the image to the region of interest. In other words, the system will ignore the data (after the centering) outside of the relevant portion of the digital image (i.e. the region of interest that may be a 460×335 pixel image) centered on the pupil. In this manner the software will avoid the need for mechanical centering devices, thereby decreasing weight and increasing system efficiency. Further some cameras may be able to only select a given region of interest in which the data of the unused portions need not be transmitted, thereby either increasing the speed of the transmission or increasing the resolution of the region of interest whereby the region of interest will be a 640×480 (or 1024×640 or 480×320 or less as desired) pixel image of the region of interest. The elimination of mechanical centering devices with one of the options above is referred to as digital centering within the meaning of this application. The high resolution digital cameras of the VOG system 10 allows the system to track and record 3-D movement of the eye (generally movement in an X-Y plane and rotational movement) and to further track pupil dilation, providing the clinician with further critical data for diagnostic testing.

The camera unit 16 also shows a location for a laser 20 which can act as a calibration system for the goggles while on the patient's head. The laser 20 will point away from the camera base or goggle base 12 and will be utilized to calibrate the system 10 such as on a wall a specific distance away. The laser 20 can also be used to monitor and control head movement. For example, the clinician may instruct the patient to maintain the visible laser image of the laser 20 on a specific point or move this image along a desired path, while the clinician can watch for variation of the laser image position from the desired location or desired path. Generally, the cap 15 will be removed and the patient asked to focus his eye on the laser image (e.g. a cross hair, or other image) on a surface a known distance away. The laser 20 is fixed relative to the head and thereby automatically eliminates head movement in this calibration step. In an occluded system the patient may not see the image of the laser 20, but the clinician can still monitor movement, and the patient need not see the laser image to move his head horizontally, vertically or maintain no movement of his head. The integrated laser 20 is a significant tool for the clinician.

The camera unit 16 may further include a pair of infrared LEDs 22 and a pair of visible light LED's 24 facing the patient. The infrared LEDs 22 allow the camera to obtain images in an occluded environment and the visible LEDs 24 allow visual stimulus to be supplied to the patient in an occluded system. The LEDs 22 and 24 can be changed in number, position, color as desired by the clinician, and can be controlled by the operator. In other words the system 10 can be easily designed to accommodate any lighting arrangement with LED's as the clinicians indicate is desirable. As an alternative, a fiber optic light can be run in front of the camera lens, to the center of the camera lens and directed at the patient whereby the patients focus on the light will also be centered on the camera. A single fiber optic strand is sufficiently thin to avoid interference with the camera image.

A key aspect to forming a portable VOG system according to the present invention is the data, the power and the control coupling for the camera unit 16. The VOG system 10 utilizes an IEEE 1394 cable, also called a firewire cable 28, for each camera unit 16. The firewire carries two twisted pair of signal wires used for data transmission and a twisted pair of power cables used for power supply. Through the use of digital cameras, low power LED elements 22 and 24 and laser 20, a 5V power supply will be sufficient. Such a power supply can be obtained from a standard laptop computer such as computer 30 shown in FIG. 7. The digital camera uses a conventional voltage regulator to step down the input voltage to 3.3 V DC. A typical firewire uses a 6-pin connection which is found on most Macintosh® Laptops, IBM® or compatible desktops and Macintosh® desktops allowing direct connection thereto. Some laptops do not have a 6 pin connection and only have a 4 pin communication link only port. A specialized adaptor can be made using a standard fire-wire adaptor (connects the four communication lines) together with a set of leads to a USB port for power. Other modifications to accommodate this arrangement may be made (e.g. replace the lead on the camera, or use an adapter, such that it can plug into the iLINK port on a SONY® VAIO which will free up the PCM-CIA and USB ports for other uses).

The system 10 provides a completely portable system 10 since the computer may be a laptop portable computer 30. A conventional laptop computer 30 weighs generally less than about 3 kilograms, and the goggles will generally weigh less than 1 kilogram (and preferably less than 300 grams and most preferably 200 grams) whereby the entire system will be much less than 8 kilograms and generally less than 5 kilograms (with current laptops the system may be about 4 kilograms). The computer 10 may also be replaced with a smaller device such as a subnotebook (not shown), which is used merely for data acquisition and control of the components (rather than analyzing and displaying the data). With the use of a smaller device the weight of the system drops even further to about 2 kilograms or less. This system would allow tests to be performed essentially anywhere and the data later transferred to a separate computer (even a desktop) for analysis and display. A portable system would be those less than about 10 kilograms, since heavier than that they will become cumbersome and unwieldy for the clinician. The system 10 is of such light weight that the system can be carried by a patient, such as on a rotational chair.

As discussed above the digital camera of the unit 16 will allow for digital centering of the patient's pupil at least in one direction. The use of digital centering eliminates the need for a mechanical adjustment mechanism (e.g. a slide) in the given direction. Using digital centering for both the X and Y directions eliminates any gross adjustment in those directions.

The VOG system according to the present invention further incorporates an EOG system that can operate independent of or preferably in conjunction with the VOG system to supplement the acquired data. The EOG system is incorporated directly into the goggle base and powered from the same source powering the digital cameras. Specifically the goggle frame 12, and the skirt thereof in particular, provide easy mounting locations for the sensors needed for conventional EOG system. The sensors can provide eye location when a patients eyes are closed, which of course the video system cannot. The firewire 28 allows for the data of the integrated EOG system to be sent to the computer 30. This data can be used to correct the eye position data of the VOG system and supplement such data when the patient's eyes are closed. An integrated EOG/VOG system will thereby provide greater accuracy in the data results and provide further testing options to a clinician in a single device. For example, one conventional diagnostic test is to examine eye position with eye closure, and the EOG/VOG system allows this test to be easily accomplished with other VOG tests. The sensors can be used to convey any physiologic data to the clinician, including but not limited to EOG data. In addition to or in place of the EOG related data the clinician may desire the sensors to convey patient temperature, blood flow data, blood pressure data, patient perspiration data, patient heart rate data, goggle position or slippage data, head position data (discussed above), light sensor (occluded systems) or any physiologic data that may be desired.

The VOG system 10 of may further include a head tracking sensor (not shown) attached to the base 12 to track and record a patient's head position. Precise position sensors are known in the art such as an inertial measurement unit from Inertial Sciences, Inc. The head position data may be used to supplement other data and possibly to assist in calculating any goggle slip that occurs, wherein knowing the goggle mass and inertia values relative to the patient and the head movement data through a head position sensor an algorithm may be developed to approximate the goggle position/slippage. Essentially the algorithm may approximate the static and kinetic friction between the skirt of the goggle base 12 and the patient and the force applied by the goggle strap and use the head position data to calculate the acceleration of the patients head and thereby approximate the goggle slippage. Calculated goggle slip can then be removed from the eye movement data through appropriate software. Another head tracking method is through use of a separate camera for recording and tracking such movement. This additional system requires a separate imaging processing for the head movement.

Figure 9:
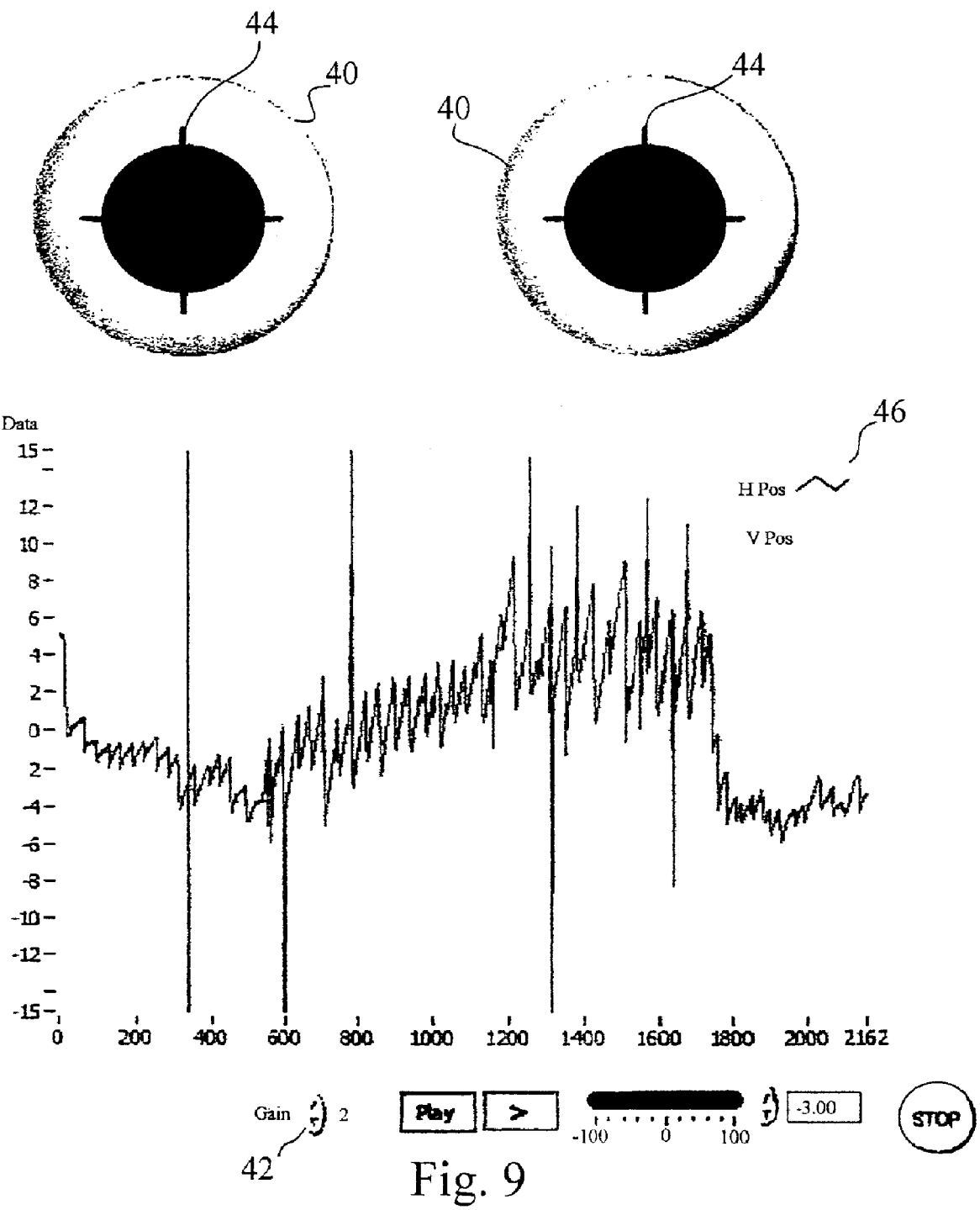
FIG. 9 is a view of one type of display available to the clinician in the VOG system according to the present invention

The VOG system 10 provides an animated eye display such as shown in FIG. 9 to the clinician to provide data in a more meaningful fashion. The details of animating an eye from given data can be found at the following website: http://user.cs.tu-berlin. de/~fidodido/StdArbeit/stdarbeit.html which shows eye animation for data playback and is incorporated herein by reference. The animated eyes 40 can more easily convey position and can include an adjustable scaling factor, or gain 42, to supplement the illustrated animated eyes. The gain is for X, Y and rotational or torsional movement (with rotation being the most difficult to accurately measure). The controllable gain 42 may be separated into the specific components if desired. The animation may include visible indicia, such as cross hairs 44, at the pupil center in front view to assist in viewing movement, in particular rotational movement. Additionally a visible line of sight can be provided in a top view. The digital image and analysis thereof for pupil center provide all the real time data needed to construct and move the animated eyes 40. The eyes 40 may also be displayed with graphical data 46.

Figure 7:
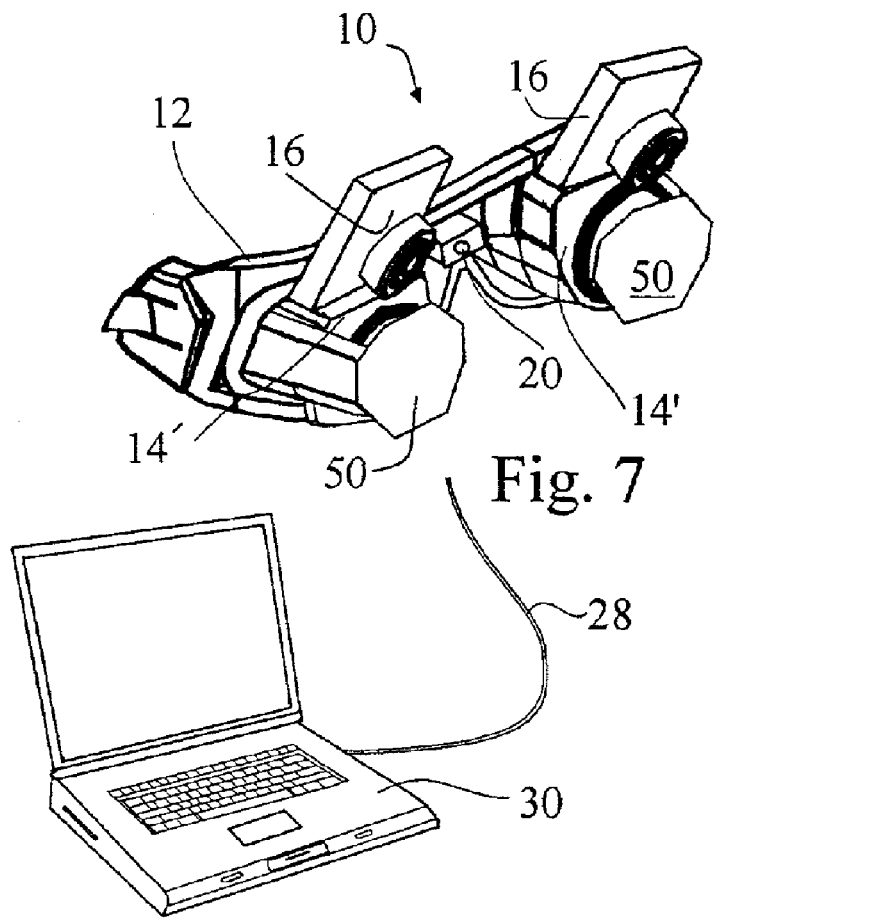
FIG. 7 is a schematic view of a top camera mounted non occluded binocular VOG system according to the present invention.
Figure 8:
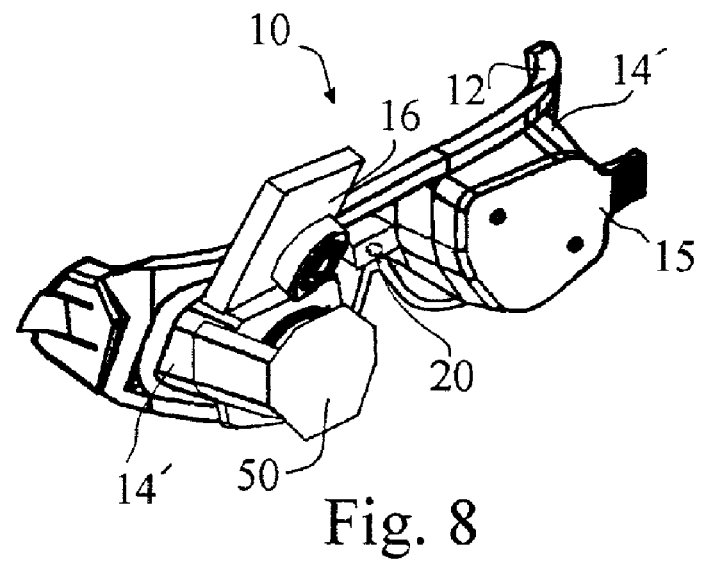
FIG. 8 is a schematic view of a top camera mounted monocular goggle for a VOG system according to the present invention.

The VOG system 10 of the present invention is intended to be a modular design. There are other high priced convertible systems such as an occluded/open face/monocular/binocular as can be found at website http://www.smi.de/3d/index.htm. However the system 10 of the present invention is modular in that the same goggle frame 12 or base is used to build occluded monocular front mounted digital camera VOG system 10 as shown in FIGS. 1-4, or binocular front mounted digital camera VOG systems, or a monocular top mounted digital camera VOG system 10 as shown in FIG. 8 (in which unit 16 is replaced with a side mounted unit 16' and a hot mirror 50 for reflecting the image into the camera), or binocular top mounted digital camera VOG system 10 as shown in FIG. 7 (with units 16', hot mirrors 50 and center mounted calibration laser 20'), or frenzel goggles with caps 15 having lenses therein, or a variety of other systems through mixing of these components and adding other modular components. As shown in FIGS. 7 and 8 the same mounting member 14' can be used for top mounted cameras 16' and for side mounted cameras wherein the mounting position of the camera and the hot mirrors would be switched. The key feature is that a wide variety of systems can be built on a single platform, the goggle frame 12. The clinician can build numerous systems through selective combinations of mounts and cameras.

Various modifications of the present invention may be made without departing from the spirit and scope thereof. For example, the system may include a digitized objective view of the lid position to provide an objective analysis for ptosis. The described embodiment is not intended to be restrictive of the present invention. The scope of the present invention is intended to be defined by the appended claims and equivalents thereto.

What is claimed is:

1. A video oculography system comprising:
   a light-weight head mounted base adapted to be attached to a patient's head;
   at least one camera attached to the base, configured to obtain video images of the patient's eye;
   a controller coupled to the at least one camera receiving and storing data signals there from;
   at least one camera light source attached to the base, wherein each camera light source is associated with one camera attached to the base and is configured to illuminate the patient's eye sufficient for the camera to obtain an image of the patient's eye; and
   at least one visual stimulus light source attached to the base and distinct from the at least one camera light source, wherein each visual light source is configured to selectively supply a visual stimulus to the patient's eye simultaneously with the camera obtaining video images of the patient's eye, wherein the at least one visual stimulus light is distinct from the camera light source.

2. The system of claim 1 wherein the light weight head mounted base is a pair of goggles.

3. The system of claim 2 wherein the goggles provide an occluded environment for the patient's eyes.

4. The system of claim 2 wherein at least two visual stimulus light sources are provided for each patient's eye.

5. The system of claim 2 wherein the camera light sources and the visual stimulus light sources are formed in an annular array for at least one of the patient's eyes.

6. The system of claim 1 further including a laser attached to the base, wherein the laser is visible to the clinician while the patient is wearing the head mounted base.

7. The system of claim 1 wherein the camera light sources have a light wavelength that is distinct from the light wavelength of the visual stimulus light sources.

8. The system of claim 7 wherein the camera light sources are infrared light sources.

9. The system of claim 1 wherein the camera light sources are formed from a plurality of infrared LEDs and the visual stimulus light sources are formed from a plurality of visible light LEDs.

10. The system of claim 1 each visual stimulus light source includes a fiber optic light.

11. The system of claim 10 wherein fiber optic light is centered on the camera.

* * * * *